United States Patent
Lee (10) Patent No.: US 11,771,720 B2
(45) Date of Patent: Oct. 3, 2023

(54) METHOD FOR PREPARING IMMUNE-TOLERIZED EXTRACELLULAR VESICLE CONTAINING LACTATE DEHYDROGENASE BAND PEROXISOME PROLIFERATOR-ACTIVATED RECEPTOR GAMMA COACTIVATOR 1-ALPHA, AND COMPOSITION COMPRISING THE EXTRACELLULAR VESICLE

(71) Applicant: STEMMEDICARE CO., LTD, Seoul (KR)

(72) Inventor: Jang Ho Lee, Seoul (KR)

(73) Assignee: STEMMEDICARE CO., LTD., Seoul (KR)

( * ) Notice: Subject to any disclaimer, the term of this patent is extended or adjusted under 35 U.S.C. 154(b) by 130 days.

(21) Appl. No.: 17/611,046

(22) PCT Filed: Aug. 29, 2019

(86) PCT No.: PCT/KR2019/011044
§ 371 (c)(1),
(2) Date: Nov. 12, 2021

(87) PCT Pub. No.: WO2020/230954
PCT Pub. Date: Nov. 19, 2020

(65) Prior Publication Data
US 2022/0305060 A1    Sep. 29, 2022

(30) Foreign Application Priority Data
May 14, 2019  (KR) .................. 10-2019-0056537

(51) Int. Cl.
*A61K 35/50*   (2015.01)
*A61P 35/00*   (2006.01)
*A61K 35/12*   (2015.01)

(52) U.S. Cl.
CPC .............. *A61K 35/50* (2013.01); *A61P 35/00* (2018.01); *A61K 2035/122* (2013.01)

(58) Field of Classification Search
CPC .... A61K 2035/122; A61K 35/50; A61P 35/00
See application file for complete search history.

(56) References Cited

U.S. PATENT DOCUMENTS

2019/0008902 A1    1/2019   Anderson

FOREIGN PATENT DOCUMENTS

| KR | 10-1820264 B1 | 1/2018 |
| KR | 10-2018-0082980 A | 7/2018 |
| KR | 10-2018-0111674 A | 10/2018 |

*Primary Examiner* — Elly-Gerald Stoica
(74) *Attorney, Agent, or Firm* — Maschoff Brennan (57) ABSTRACT

The present invention relates to anticancer extracellular vesicles, a preparation method therefor, and an anticancer composition comprising same. Immune-tolerized extracellular vesicles containing LDHB and PGC-1α of the present invention provide cancer treatment, suppression of cancer metastasis, and cancer prevention technologies by normalizing cancer cell-specific aerobic glycolysis energy metabolic pathway in which lactate and hydrogen ions, which form a tumor microenvironment favorable for immune evasion, proliferation, metastasis and invasion of cancer cells, are produced, thereby enabling tumors to be effectively removed by means of the immune system of a patient.

9 Claims, 3 Drawing Sheets

METHOD FOR PREPARING IMMUNE-TOLERIZED EXTRACELLULAR VESICLE CONTAINING LACTATE DEHYDROGENASE BAND PEROXISOME PROLIFERATOR-ACTIVATED RECEPTOR GAMMA COACTIVATOR 1-ALPHA, AND COMPOSITION COMPRISING THE EXTRACELLULAR VESICLE

TECHNICAL FIELD

The present invention relates to an anticancer extracellular vesicle, a method for preparing the same, and an anticancer composition including the same, more particularly, an anticancer extracellular vesicle, including: (i) lactate dehydrogenase B (LDHB), (ii) peroxisome proliferator-activated receptor gamma co-activator 1-alpha (PGC-1α), and (iii) calcium calmodulin-activated kinases type 1B (CaMK1B), calcium calmodulin-activation kinases type 2B (CaMK2B), calcium calmodulin-activated kinases type 5 (CaMK5), myocyte specific enhancer 2B (MEF2B), myocyte specific enhancer 2C (MEF2C), and cyclin adenosine monophosphate (cAMP), a preparation method thereof, and an anticancer composition including the same.

BACKGROUND ART

Common and main features of tumor microenvironment, in which immune evasion, proliferation, metastasis and invasion of cancer cells occur, may be summarized as a high lactic acid ("lactate") concentration and a low pH environment. This is a result of energy metabolism specific to cancer cells. In particular, a solid cancer proceeds energy metabolism in a manner known as "Warburg Effect" in order to survive in an environment where glucose and oxygen essential for cancer cell metabolism are hardly supplied from blood vessels. The "Warburg Effect" is a theory proposed in the 1920s, demonstrating that, despite a high oxygen concentration, cancer cells prefer a mechanism of lactate and adenosine triphosphate (ATP) production by aerobic glycolysis of pyruvic acid ("pyruvate") rather than ATP production by oxidative phosphorylation (OXPHOS) in mitochondria, which occurs in normal cells. At the beginning of the disclosure, the above theory was known as a metabolic phenomenon due to dysfunction of mitochondria, however, subsequent studies revealed several reasons why cancer cells utilize inefficient aerobic glycolysis in terms of ATP production. That is, (1) survival in hypoxic conditions through metabolism independent of oxygen concentration; (2) intermediate metabolites of aerobic glycolysis-nicotinamide adenine dinucleotide phosphate (NADPH), glutamine, etc.—are utilized to continuously activate diverse signal transduction systems in relation to the antioxidation defense mechanism and continuous proliferation of cancer cells such as synthesis of fatty acids as an alternative energy source and, at the same time, to act to inhibit cancer cell aging and death. In addition, lactate and hydrogen ions produced as metabolites of aerobic glycolysis are substances in situ threatening survival of cancer cells, which are secreted to the outside of cancer cells by various membrane transportation proteins and thus act as an important element to form a tumor microenvironment such as cancer invasion or immune evasion. For example, lactate secreted to the outside of cells may promote expression of vascular endothelial growth factor (VEGF) thereby accelerating generation of new blood vessels to receive nutrients and oxygen, as well as cancer cell migration and metastasis. Further, the secreted lactate contributes to deterioration of activity of immune cells such as reduction of T cell activity and cytotoxicity, reduction of inflammatory cytokine secretion, reduction of monocyte migration, or the like, through induction of pH environment, thereby playing a role of protecting cancer cells from the immune system.

More specifically, when cytotoxic T cells and helper T cells are activated in the tumor microenvironment, these are rapidly proliferated through aerobic glycolysis in a similar manner to cancer cells. Although lactate and hydrogen ions generated during the above metabolism must be secreted outside T cells, these cannot be normally discharged due to high concentrations of lactate and hydrogen ions already present in the tumor microenvironment, which may lead to natural death of T cells. Further, since the secretion of some granulates such as granzyme, perforin, etc., which directly dissolve cancer cells under low pH and glucose deficient and hypoxic conditions and interferon-gamma is considerably reduced, and LHD5 protein (consisting of four (4) LDHA subunits) synthesized by lactate dehydrogenase A (LDHA), which was activated by hypoxia inducible factor (HIF-1α) over-expressing in cancer cells, inhibits expression of natural killer group 2D (NKG2D) receptor in NK cells, thereby reducing immunity monitoring function by NK cells.

Dendritic cells (DC) are also converted into tumor associated dendritic cells (TADCs) phenotype in a tumor microenvironment where low pH and high lactate concentration are maintained, in order to reduce expression of co-stimulatory molecules such as CD80, CD86 and CD40, or the like. Further, DC may induce differentiation into regulatory DCs and/or regulatory T cells that reduce secretion of IL-12 as an inflammatory cytokine while secreting anti-inflammatory cytokines (IL-10, IL-6, TGF-β), chemokines (CCL-2, CXCL1, CXCL5), VEGF, GM-CSF (Granulocyte-macrophage colony stimulating factor) and prostaglandin E2 (PGE2) so as to lead to immune-tolerant environments, while promoting secretion of immunosuppressive factors from the above cells, thereby having a significant role in constructing the tumor microenvironment. Like the T cells, the DCs also conduct aerobic glycolysis in the process of maturation and activation. Further, lactate and hydrogen ions produced as metabolites are not properly secreted out of the DCs in the tumor microenvironment, hence causing metabolic dysfunction.

Further, in the tumor microenvironment under low pH and high lactate concentration, the differentiation of myeloid cells into myeloid-derived immunosuppressor cells (MDSC), which inhibit cytotoxicity and activity of T cells and NK cells, is accelerated. In particular, macrophages may also be promptly differentiated into M2-type tumor-associated macrophages (TAM) phenotype that secretes immune-tolerant cytokines-TNF, IL-6, IFN-γ and IL-1β. In this process, the cells continuously survive and are accumulated in the tumor microenvironment through aerobic glycolysis similar to cancer cells, thus contributing to maintain low pH and high lactate concentration environments.

On the other hand, monoclonal antibodies, which have recently attracted attention in treatment of various solid cancers, recognize Fc sequence of the antibody through the binding of a target antigen specifically expressed in tumors or immune cells to Fc receptors (FcR) and thus remove the same from the immune system through phagocytosis, complement-dependent cytotoxicity and antibody-dependent cytotoxicity, thereby exhibiting therapeutic effects. At low pH, the antibody is degraded by oxidation and Fc aggregation, causing deterioration in binding activity of the antibody to the antigen. Further, a histidine residue at an interaction site of bio-molecules may be protonated under low pH condition to thus increase dissociation, resulting in deterioration in binding affinity between Fc-FcR and eventually reduction of therapeutic effects. The above results can also be confirmed from the fact that anti-tumor response of immune checkpoint inhibitor (ICI) to cytotoxic T-lymphocyte associated protein 4 (CTLA-4) or programmed death ligand 1 (PD-L1), which have recently attracted attention, is increased when neutralizing tumor acidity.

As described above, low extracellular pH in the tumor microenvironment formed by secretion of lactate and hydrogen ions, which are metabolites of cancer cell-specific aerobic glycolysis, to the outside of cancer cells, the resulting pH gradient across a tumor cell membrane, high lactate concentration and low oxygen tension may act as barriers against delivery and efficacy of active ingredients, wherein the active ingredients include: diverse chemotherapeutic agents for solid cancer; immune checkpoint inhibitors targeting co-stimulatory molecules of cytotoxic T lymphocytes, for example, CTLA-4 or PD-L1; immunotherapies including, for example, chimeric antigen receptor T cells (CAR-T cells) resulting from genetic operation of T cell receptors that target specific tumor surface antigens (T cell receptor, TCR); monoclonal antibody therapeutics, or the like, whereby the above factors have only very limited effects on cancer. Further, for cancer-specific energy metabolism, LDHA enzyme that converts pyruvate into lactate in cancer cells, a monocarboxylate transporter (MCT) that secretes lactate and hydrogen ions generated in cancer cells to the outside of cancer cells, etc. were targeted and research thereof has been conducted, however, there is a concern about side effects such as metabolic disturbance of normal cells, and studies on normalization of entire tumor microenvironments to treat cancer have yet to proceed.

Therefore, the inventors of the present invention have designed a treatment mechanism on the ground that, if normalizing aerobic glycolysis specific to cancer cells to secret hydrogen ions and lactate, which have a key role in construction of tumor microenvironment, the secretion of hydrogen ions and lactate may be suppressed and a barrier based on the tumor microenvironment would collapse and, finally, immune signals disturbed by lactate and low pH in the tumor microenvironment would be normalized, whereby patient's own immune cells could effectively remove tumor and cancer cells. Therefore, in order to realize the above idea, a pharmaceutical composition for cancer treatment with so-called "Reverse Warburg Effect" as a reaction mechanism, including active ingredients, specifically: LDHB immediately reducing lactate generated excessively in cancer cells by "Warburg Effect" into pyruvate; and extracellular vesicles that contain PGC-1α having a role of maintaining homeostasis of intracellular lactate by inhibiting the expression of LDHA in cells and activating LDHB has been developed. However, when in vitro culturing cells derived from autologous or other substances to produce extracellular vesicles, these have immunogenicity that causes harmful immune responses by heterologous antigens and disturbed immune signals. Therefore, in order to primarily eliminate the above problem, a method for production of immune-tolerized extracellular vesicles will be essentially involved.

The immune system of a human body prevents internal environment of a living body from being disturbed by foreign or endogenous foreign materials (also called antigens) to maintain a constant state at all times, and various cells in the body occur different immune responses to remove the antigens. In particular, in the case where autologous or homogenous cells or tissues/organs, transplanted cells or tissues/organs act as immunogenicity due to major histocompatibility complex (MHC) antigen mismatch between a donor and a recipient, which in turn derive an immune response from the immune system of the recipient. Further, like the transplanted cells or tissues/organs, extracellular vesicles secreted from cells also act as immunogenicity due to antigen-presenting molecules (MHC Class I or Class II molecules) of origin cells present in the same double phospholipid membrane as a cell membrane of the origin cells, thereby triggering immune responses.

DISCLOSURE

Technical Problem

Therefore, the present inventors have believed that, in order for extracellular vesicles, which are a main component of a composition for cancer treatment according to the present invention, to approach a tumor microenvironment and bind to cancer cells without occurrence of immune response by immunogenicity in situ so as to exhibit anti-cancer efficacy, it would be very important to prepare immune-tolerized extracellular vesicles containing HLA-G protein that constructs an immune-tolerant environment to completely protect the fetus from the maternal immune system during pregnancy. To this end, first, we established in vitro culture conditions that simulate culture characteristics and in vivo environment of trophoblasts that continuously secret HLA-G protein on the maternal-fetal interface during pregnancy, and induced immune-tolerant characteristics in target cells, with which extracellular vesicles for cancer treatment are produced, according to the above establishment. It was confirmed that the immune-tolerized extracellular vesicles secreted therefrom do not cause an immune rejection reaction due to their own immunogenicity and, at the same time, extracellular vesicles for cancer treatment including: LDHB, which directly converts lactate into pyruvate; and PGC-1α, which maintains homeostasis of lactate, are completely protected from an immune system of a patient, and pass through the tumor microenvironment and are transferred to the cancer cells to normalize energy metabolism of the cancer cells and eventually demonstrate cancer treatment effects, thereby completing the present invention.

Technical Solution

In order to solve the above problems, one object of the present invention is to provide extracellular vesicles, including: (i) lactate dehydrogenase B (LDHB); (ii) peroxisome proliferator-activated receptor gamma co-activator 1-alpha (PGC-1α), and (iii) calcium-calmodulin activated kinases type 1B (CaMK1B), calcium-calmodulin activated kinases type 2B (CaMK2B), calcium-calmodulin activated kinase type 5 (CaMK5), myocyte specific enhancer 2B (MEF2B), myocyte specific enhancer 2C (MEF2C) and cyclin adenosine monophosphate (cAMP).

Another object of the present invention is to provide a pharmaceutical composition for inhibiting cancer metastasis, preventing or treating cancer, which includes the extracellular vesicles described above.

A still further object of the present invention is to provide a method for preparation of the extracellular vesicles described above.

Advantageous Effects

Immune-tolerized extracellular vesicles containing LDHB and PGC-1α according to the present invention are characterized by changing cancer cell-specific aerobic glycolysis energy metabolic pathway, wherein lactate and hydrogen ions to form tumor microenvironments favorable for immune evasion, proliferation, metastasis and invasion of cancer cells are generated, into normal cells ("normalization"), whereby anticancer treatment, cancer metastasis suppression and cancer prevention techniques capable of efficiently removing tumors owing to an immune system of a patient can be provided.

BEST MODE

One aspect of the present invention to solve the above problems is to provide extracellular vesicles, including: (i) lactate dehydrogenase B (LDHB); (ii) peroxisome proliferator-activated receptor gamma co-activator 1-alpha (PGC-1α), and (iii) calcium-calmodulin activated kinases type 1B (CaMK1B), calcium-calmodulin activated kinases type 2B (CaMK2B), calcium-calmodulin activated kinase type 5 (CaMK5), myocyte specific enhancer 2B (MEF2B), myocyte specific enhancer 2C (MEF2C) and cyclin adenosine monophosphate (cAMP).

Further, (iv) HLA-G1 and HLA-G5 proteins, and (v) human chorionic gonadotropin (hCG) and placental growth factor (PlGF) may be additionally contained in the extracellular vesicles.

Figure 3:
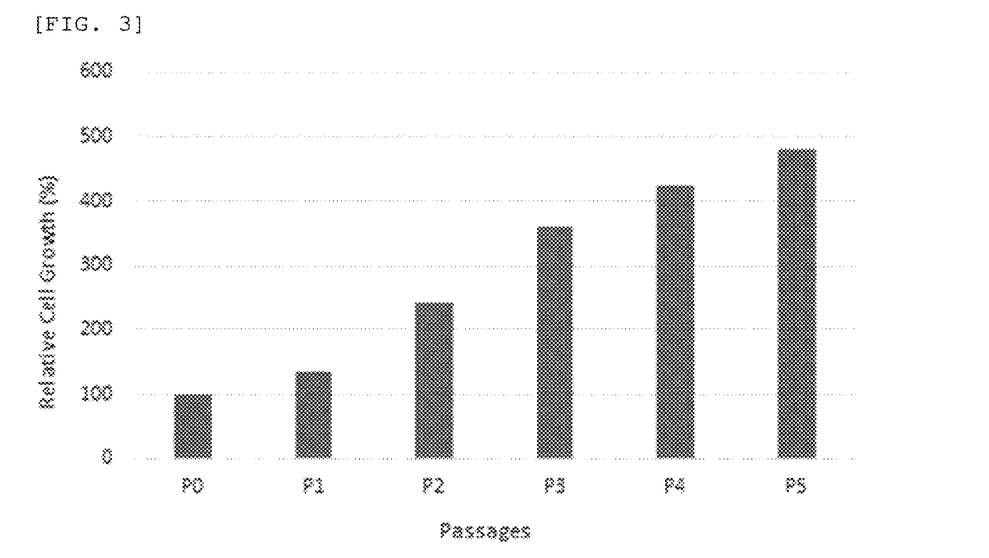
FIG. 3 is a graph showing cell growth rates in the culture of trophoblasts in an in vitro culture matrix gel prepared to establish trophoblasts having immune-tolerant properties that always express HLA-G protein.
Figure 4:
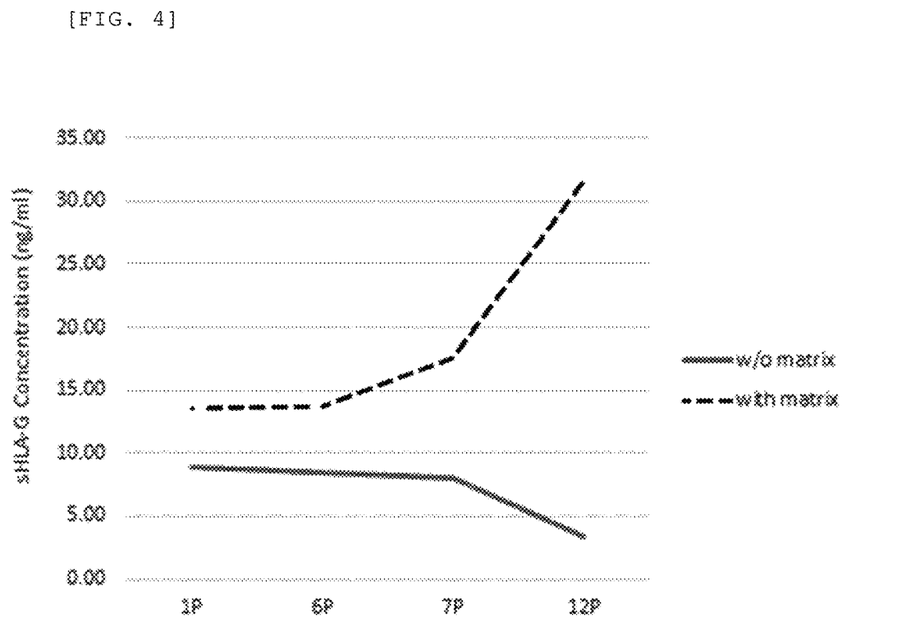
FIG. 4 is a graph showing concentrations of HLA-G5 protein present in the culture supernatant of trophoblasts cultured in an in vitro culture matrix gel prepared to establish trophoblasts having immune-tolerant properties that always express HLA-G protein.
Figure 5:
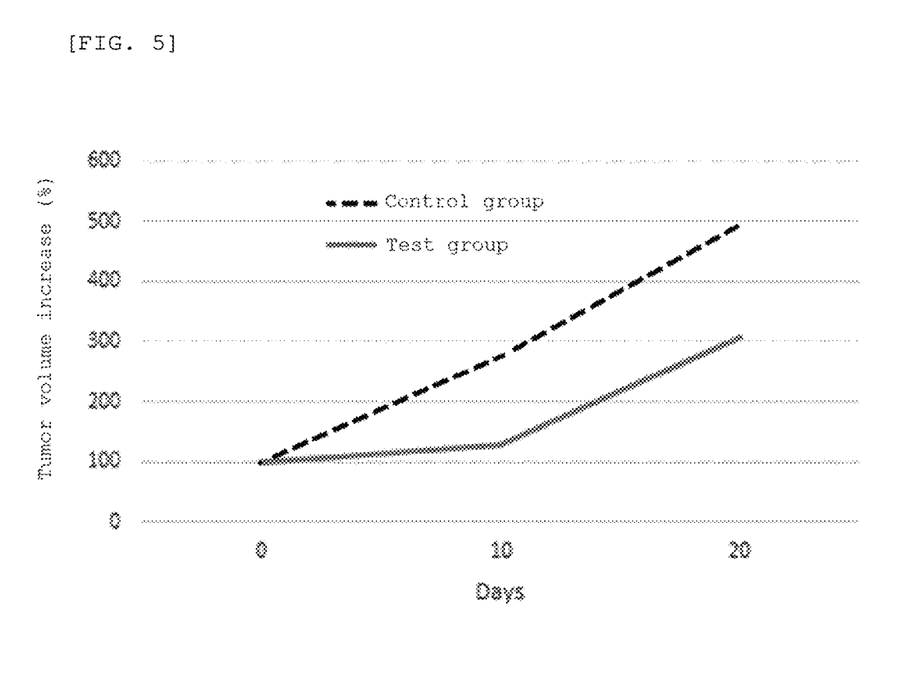
FIG. 5 is a graph showing effects of inhibiting cancer growth by extracellular vesicles through a change in tumor size by treating a mouse model with the extracellular vesicles having immune-tolerant properties.

In a specific embodiment of the present invention, a matrix gel for in vitro culture of ("in vitro culture matrix gel") of trophoblasts in which a human amniotic membrane and amniotic fluid-derived mesenchymal stem cells were replaced with fetal bovine serum, may be prepared to confirm continuous growth of trophoblasts (FIG. 3), and continuous secretion of sHLA-G protein were confirmed by measuring the culture supernatant obtained during subculture (FIG. 4). Further, extracellular vesicles derived from trophoblasts may be prepared for transcription of immune-tolerant properties to target cells (Table 2), and immune-tolerized anticancer extracellular vesicles containing LDHB, PGC-1α, and PGC-1α mRNA transcription promoters, which are active ingredients for cancer treatment and prevention, may be prepared (Table 3). Further, in order to determine whether the prepared anticancer extracellular vesicles are absorbed by cancer cells, an absorption rate into breast cancer cell lines were measured (Table 4), and it was confirmed that the extracellular vesicles prepared in a mouse cancer model have effects of decreasing tumor size (FIG. 5).

The term "extracellular vesicles" of the present invention refers to vesicular bodies produced in cells and secreted out of the cells and includes, but not limited to, exosomes, microvesicles, microparticles, and the like.

In the present invention, the extracellular vesicles are proposed to avoid immune responses by different immune cells present in the immune system of a patient and a tumor microenvironment so that active ingredients can be sufficiently delivered to cancer cells, and may include various factors so as to have anticancer activity. Specifically, the extracellular vesicles of the present invention may include all of: lactate dehydrogenase B (LDHB), which directly converts lactate in cancer cells into pyruvate; peroxisome proliferator-activated receptor gamma co-activator 1-alpha (PGC-1α) that maintains homeostasis of lactate in cancer cells; and transcription factors promoting PGC-1α mRNA expression, specifically, calcium-calmodulin activated kinases type 1B (CaMK1B), calcium-calmodulin activated kinases type 2B (CaMK2B), calcium-calmodulin activated kinases type 5 (CaMK5), myocyte specific enhancer 2B (MEF2B), myocyte specific enhancer 2C (MEF2C) and cyclin adenosine monophosphate (cAMP).

The term "lactate dehydrogenase (LDH)" of the present invention refers to an enzyme involved in the inter-conversion reaction of pyruvate and lactate degraded through glycolysis of glucose in cells, and may include two subunits, LDHA and LDHB. LDHA enzyme is associated with conversion of pyruvate into lactate. On the contrary, LDHB enzyme is associated with conversion of lactate into pyruvate. In particular, in the case of cancer cells, LDHA enzyme is over-expressed whereas LDHB is suppressed, whereby the conversion of pyruvate into lactate occurs very actively. On the other hand, LDHB enzyme is expressed in the liver or kidney and plays an important role in gluconeogenesis, that is, a metabolism of converting lactate into pyruvate and then synthesizing glucose again. Moreover, this enzyme is also expressed in heart tissues or neurons to convert lactate into pyruvate, thereby having a role of utilizing lactate as a nutrient for oxidative metabolism.

In the present invention, the LDHB is used for avoiding cancer cell immunity while normalizing high lactate concentration and low pH, which are characteristics of the surrounding microenvironment.

The term "peroxisome proliferator-activated receptor gamma co-activator 1-alpha (PGC-1α)" of the present invention refers to a co-activator involved in various metabolic processes that are very important in cells, and may be bound to different types of nuclear receptors to act as a co-activating factor for metabolic processes such as: promotion of mitochondrial biosynthesis; increase of related gene expression; promotion of glucose energy metabolism; and increase in fatty acid oxidation and antioxidant enzyme expression, etc., while rapidly promoting PGC-1α mRNA expression through a signal cyclical pathway, simultaneously. Specifically, in energy metabolism related to lactate, more specifically, when PGC-1α binds to estrogen-related receptors alpha (ERRα), LDHB mRNA expression in cells increases, while having a role of suppressing LDHA mRNA expression to maintain lactate homeostasis when combined with retinoid-X receptor (RXR). Further, when combined with nuclear respiratory factors (NRFs), oxidative metabolism action through mitochondria (OXPHOS) may be activated. In the present invention, the PGC-1α is responsible for increasing LDHB expression.

Figure 2:
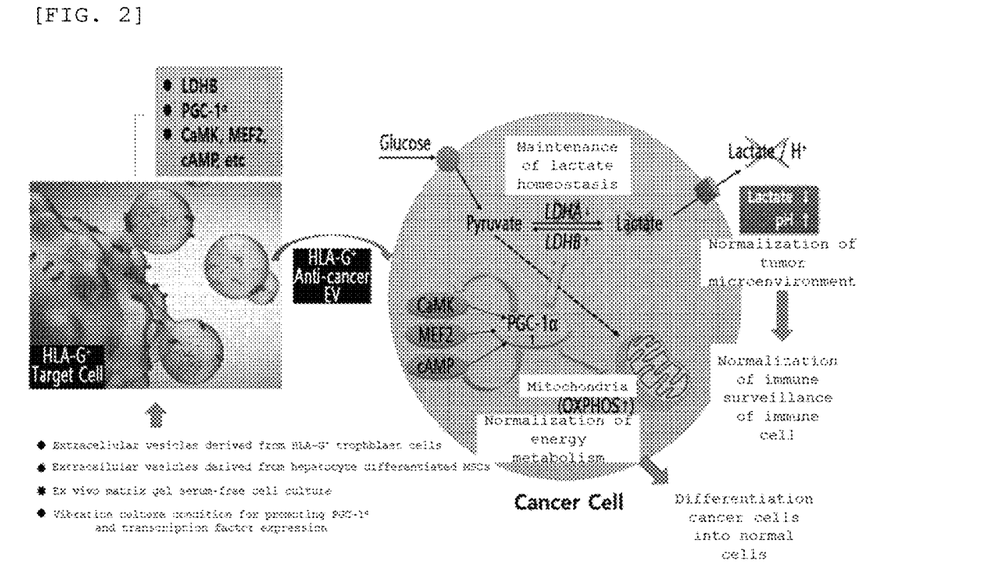
FIG. 2 is a schematic diagram illustrating a cancer treatment mechanism by immune-tolerized extracellular vesicles containing all of transcription promoting factors that accelerate LDHB, PGC-1α and PGC-1α mRNA expressions.

Therefore, the present inventors have presumed that: if not only LDHB involved in direct conversion of lactate into pyruvate but also PGC-1α, which functions to maintain lactate homeostasis in cells, and extracellular vesicles containing various factors increasing mRNA expression of PGC-1α are applied to cancer cells, the conversion of pyruvate into lactate may be reduced due to increase in LDHB expression and inhibition of LDHA expression in the cancer cells and, at the same time, the conversion of lactate into pyruvate may be accelerated to thus reduce production and secretion of lactate and hydrogen ions, which in turn normalizes the function of immune cells in the tumor microenvironment, thereby effectively eliminating canner cells and tumors. At the same time, it was presumed that energy metabolism in cancer cells may also be converted from aerobic glycolysis to oxidative metabolism in mitochondria by promoting the expression of PGC-1α, in which mRNA expression is activated by various transcription factors, thereby achieving normalization and treatment of cells. The mechanism of cancer treatment by extracellular vesicles containing LDHB, PGC-1α, and PGC-1α mRNA transcription promoters proposed by the present inventors is shown in FIG. 2.

In a specific embodiment of the present invention, on the basis of the assumption that the expression of PGC-1α will be mostly promoted by an increase in intracellular lactate concentration as well as exercise stimulation in muscle cells, in order to produce extracellular vesicles for cancer treatment which contain PGC-1α and transcription factors to promote PGC-1α mRNA expression, culturing target cells were implemented under continuous vibration conditions on an in vitro culture matrix gel containing polylactic acid. As a result, it was confirmed that the extracellular vesicles obtained through serum-free culture of the target cells contained PGC-1α and transcription factors promoting expression of PGC-1α mRNA (Table 3).

At this time, the transcription factors promoting PGC-1α mRNA expression may include, specifically, thyroid hormone (TH), nitric oxide synthase (NOS), p38 mitogen-activated protein kinase (p38MARK), sirtuines (SIRTs), calcineurin, calcium-calmodulin activated kinases (CaMKs), adenosine monophosphate activated kinase (AMPK), cyclin dependent kinases (CDKs), myocyte specific enhancer 2 (MEF2) and beta adrenergic stimulation (β/cAMP), but it is not particularly limited as long as the transcription factor is a protein to promote PGC-1α expression in cells.

Specifically, calcium-calmodulin activated kinases type 1B (CaMK1B), calcium-calmodulin activated kinases type 2B (CaMK2B), calcium calmodulin activated kinase type 5 (CaMK5), myocyte specific enhancer 2B (MEF2B), myocyte specific enhancer 2C (MEF2C) and cyclin adenosine monophosphate (cAMP) may have a role of promoting the expression and transcription of PGC-1α mRNA.

In the present invention, the extracellular vesicles may be immune-tolerized. Specifically, the term "immune tolerance" of the present invention, also referred to as immunological tolerance, means a state in which an immune response to a specific antigen is not exhibited. The immune tolerance of the present invention may be implied by HLA-G treatment, but is not limited thereto The term "trophoblast" of the present invention refers to a type of cells to form the placenta, and may provide signaling and nutrients relevant to embryonic development to an inner cell mass in the early stage of development.

Further, the trophoblast is an important cell that occurs immune tolerance to protect fertilized embryo from the material immune system so as to induce successful implantation and, thereafter, may form the placenta and continuously secrete the progesterone hormone, thereby having a significant role of maintaining pregnancy and development of the fetus. As such, it is known that the role of trophoblasts is based on the secretion and expression of HLA-G protein.

As used herein, the term "HLA-G protein" refers to a protein called human leukocyte antigen G or HLA-G histocompatibility antigen class G, etc. This protein was first discovered in extravillous trophoblasts (EVT) present at the maternal-fetal interface during pregnancy, and is a heterologous material (membrane-bound HLA-G, such as HLA-G1, G2, G3 and G4 are present) that is expressed only in the cellular membrane by selective conjugation of HLA-G mRNA, and has a single molecular form in a soluble state to be secreted to the outside of the cells (HLA-G5, G6 and G7 are present as soluble HLA-G).

In the present invention, the HLA-G protein has low polymorphism and specificity to act on immune cells, thereby reducing toxicity of immune cells and promoting differentiation of regulatory T cells, whereby this protein has an essential role in establishment of an immune-tolerant environment in order to protect the fetus, which is a half-allograft from the maternal immune system, especially during pregnancy.

Specifically, membrane-bound HLA-G molecules may be combined with immunoglobulin-like transcription (ILT)2 receptors, which are expressed on natural killer (NK) cells, T cells, B cells, dendritic cells (DC), monocytes and macrophages, so as to inhibit cytotoxicity, immune cell proliferation and antibody formation; may be combined with ILT4 receptors in bone marrow cells, monocytes and DCs to reduce antigen presentation and inflammatory cytokine secretion; may be combined with killer-cell immunoglobulin-like receptors (KIR2DL4) and CD8 receptors to induce reduction of cytotoxicity of immune cells and death thereof, therefore, the above molecules may have a role of inducing short-term immune tolerance according to the above-listed reactions. In particular, the soluble HLA-G5 molecules secreted from trophoblasts during pregnancy may promote the differentiation into regulatory T cells and tolerogenic DC cells having immune-tolerant properties, thereby inducing a long-term immune-tolerant environment so as to maintain normal pregnancy. Until now, although a mechanism of HLA-G expression restricted to trophoblasts in healthy conditions has not been fully elucidated, it is known that regulatory base sequences such as an interferon-stimulating response factor (ISRE), a heat shock factor (HSE), a hypoxic response factor (HRE) and, specifically, a progesterone reaction factor (PRE) which is distinguished from other HLA class I, etc., are present in a regulatory region of HLA-G5' gene. Thereamong, ISRE, HSE and HRE are regions to be activated in stressful situations such as inflammation and hypoxic conditions, wherein HLA-G may be expressed in pathological conditions such as cancer or infection and in bone marrow-derived mesenchymal stem cells stimulated by interferon-gamma. Therefore, the present inventors hypothesized that progesterone, a hormone mainly secreted during implantation and pregnancy, may play an important role as a factor capable of promoting mRNA expression of HLA-G in a non-stress environment.

The term "progesterone" of the present invention refers to a kind of female hormone, which regulates the female reproductive cycle along with follicle stimulating hormone (FSH), luteinizing hormone (LH) and estrogen. Initially, this hormone is secreted from the corpus luteum and keeps the endometrium thick so that the fertilized egg may be normally implanted and, after implantation, is secreted from the placenta and maintains a higher thickness of the uterine wall in order to maintain normal pregnancy.

In the present invention, the progesterone promotes HLA-G protein mRNA expression in the trophoblasts, and the secretion of progesterone in the luteal may be accelerated by human chorionic gonadotropin (hCG) secreted from the trophoblasts generated outside the embryo, while the secretion of progesterone in the placenta is stimulated by hCG and the placental growth factor (PlGF).

Specifically, HLA-G secretion characteristics of the trophoblasts, that is, secretion of HLA-G protein while being actively and continuously proliferated and differentiated by hCG and progesterone in the process of continuous invasion into maternal decidual tissues at the maternal-fetal interface, as well as proliferation characteristics of the trophoblasts in which pH around the cells was significantly lowered compared to other cells when lactate and hydrogen ions generated by aerobic metabolism of the trophoblasts were secreted out of the cells, have been demonstrated.

Figure 1:
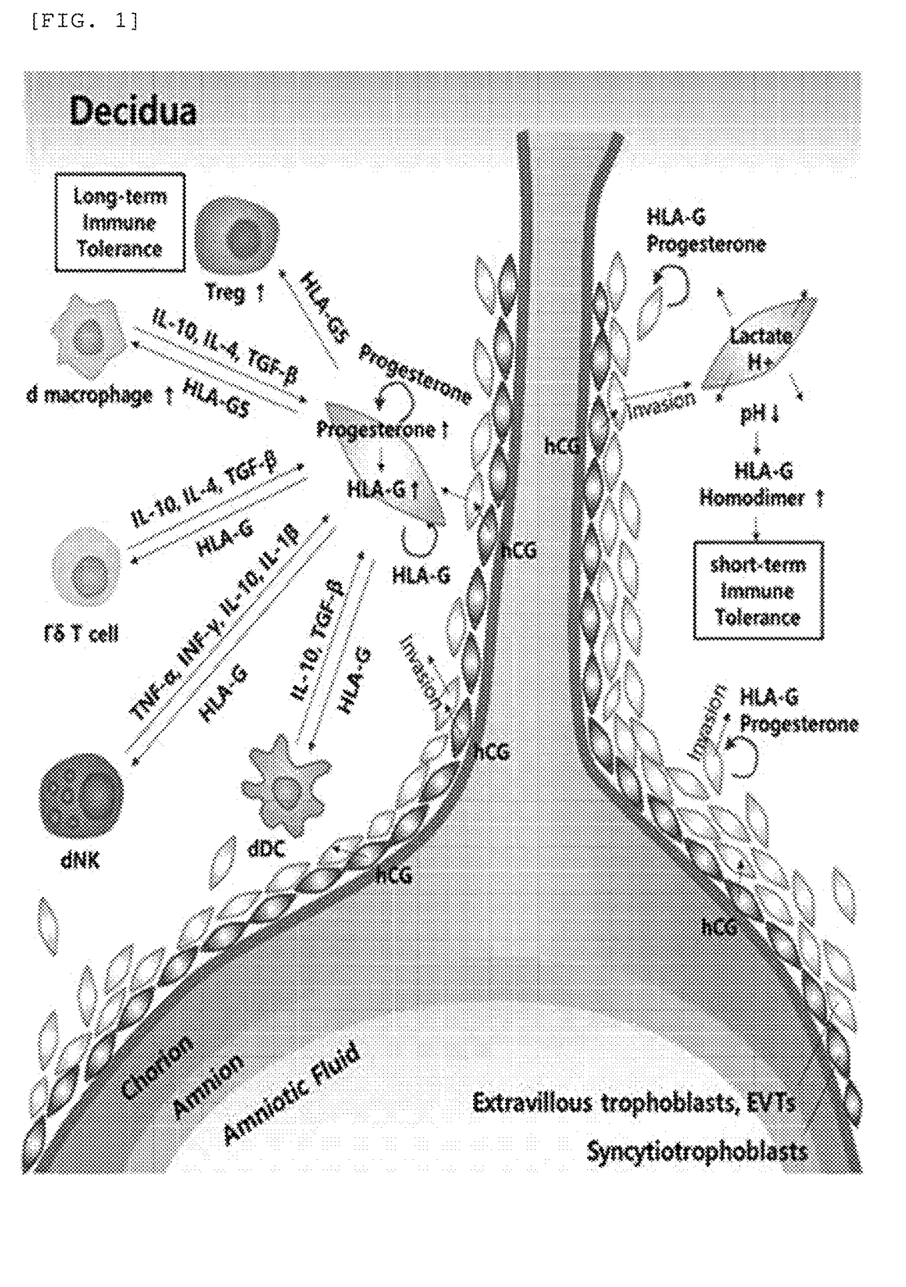
FIG. 1 is a schematic diagram illustrating assumptions to provide in vitro culture conditions that simulate the environment at the maternal-fetal interface during pregnancy, so as to establish trophoblasts having immune-tolerant properties that always express HLA-G protein.

In addition, in order for trophoblasts to continuously secrete and express HLA-G protein at the maternal-fetal interface, it was hypothesized that cytokines such as interleukin-1 beta (IL-1β), interleukin-6 (IL-6), interleukin-10 (IL-10), transforming growth factor beta (TGF-β), interferon-gamma (IFN-γ) and tumor necrosis factor alpha (TNF-α) secreted by interaction between the trophoblasts and various immune cells present in the deciduous membrane would have very important roles. Further, the fetus exists in the amniotic fluid surround by the amniotic membrane during pregnancy, and the fetal membrane is composed of the amnion and the chorion in which the trophoblasts are present, and the placenta consists of a fetal-derived chorionic membrane and the maternal decidual membrane. The present inventors have devised a matrix gel for in vitro culture of trophoblasts including extracellular vesicles derived from human amniotic fluid and amniotic membrane stem cells in order to simulate in vitro a fetal membrane structure during pregnancy. As described above, the assumption for in vitro culture conditions in order to induce the secretion and expression characteristics of HLA-G protein in the trophoblasts has been summarized in FIG. 1.

Therefore, the extracellular vesicles of the present invention may further include HLA-G1 and HLA-G5 proteins causing immune tolerance, as well as human chorionic gonadotropin (hCG) and placental growth factor (PlGF) that activate progesterone to promote mRNA expression of HLA-G protein.

In another aspect, the present invention provides a pharmaceutical composition for inhibiting cancer metastasis, preventing or treating cancer, which includes the extracellular vesicles.

Further, in another aspect, the present invention provides use of the extracellular vesicles for inhibiting cancer metastasis.

The extracellular vesicles are as described above, and more specifically, the anticancer extracellular vesicles according to the present invention may include LDHB enzyme as an enzyme that instantly converts lactate in cancer cells into pyruvate and returns to an energy metabolism manner of normal cells, may further contain PGC-1α to maintain homeostasis of lactate in cancer cells and various transcription promoting factors to promote the expression of and PGC-1α mRNA. Further, the extracellular vesicles of the present invention may express HLA-G1 and HLA-G5 proteins, which have immune-tolerant properties and can directly bind to cancer cells through a tumor microenvironment, without inducing an immune response due to immunogenicity of the extracellular vesicles in situ. Therefore, as described above, by normalizing high lactate concentration and low pH environments that establish the tumor microenvironment implying desirable conditions for proliferation, metastasis and invasion of cancer cells, anticancer effects of effectively eliminating the tumor from the immune system of a patient can be demonstrated.

As used herein, the term "cancer" refers to a tumor that grows abnormally or a disease that forms a tumor due to autonomic excessive growth of body tissues.

Specifically, the cancer may include, for example, lung cancer (e.g., non-small cell lung cancer, small cell lung cancer, malignant mesothelioma), mesothelioma, pancreatic cancer (e.g., pancreatic duct cancer, pancreatic endocrine tumor), pharyngeal cancer, laryngeal cancer, esophageal cancer, gastric cancer (e.g., papillary adenocarcinoma, mucinous adenocarcinoma, adenosquamous carcinoma), duodenal cancer, small intestine cancer, bowel cancer (e.g., colon cancer, rectal cancer, anal cancer, familial colon cancer, hereditary nonpolyposis colon cancer, gastrointestinal interstitial tumor), breast cancer (e.g., invasive ductal cancer, noninvasive ductal cancer, inflammatory breast cancer), ovarian cancer (e.g., epithelial ovarian carcinoma, extra-testicular germ cell tumor, ovarian germ cell tumor, ovarian hypomalignant tumor), testicular tumor, prostate cancer (e.g., hormone-dependent prostate cancer, hormone-independent prostate cancer), liver cancer (e.g. hepatocellular carcinoma, primary liver cancer, extrahepatic bile duct cancer), thyroid cancer (e.g., medullary thyroid carcinoma), kidney cancer (e.g., renal cell carcinoma, transitional epithelial carcinoma of the renal pelvis and ureters), uterine cancer (e.g. cervical cancer, endometrial cancer, uterine sarcoma), brain tumors (e.g. medulloblastoma, glioma, pineal gonadoblastoma, pemphigoid gonadoblastoma, diffuse gonadomatosis, degenerative gonadoblastoma, pituitary adenoma), retinoblastoma, skin cancer (e.g., basal cell carcinoma, malignant melanoma), sarcoma (e.g. rhabdomyosarcoma, leiomyosarcoma, soft tissue sarcoma), malignant bone tumor, bladder cancer, hematologic cancer (e.g., multiple myeloma, leukemia, malignant lymphoma, Hodgkin disease, chronic bone marrow proliferative disease), primary unknown cancer, and the like, and more specifically, may be breast cancer and colon cancer, but it is not limited thereto.

The term "prevention" of the present invention refers to any action of inhibiting or delaying the growth and metastasis of a tumor by the conjugate according to the present invention.

The term "treatment" of the present invention refers to any action in which symptoms of tumor growth and metastasis are improved or beneficially altered by the conjugate.

In the present invention, the composition is preferably used in humans, but may also be used for livestock such as cows, horses, sheep, pigs, goats, camels, antelope, dogs or cats, in which any inflammatory disease or cancer occur and cancer may be suppressed or reduced by administration of the composition according to the present invention.

With regard to the pharmaceutical composition for preventing or treating cancer according to the present invention, an administration route and an administration method of the composition are not particularly limited, and any administration route and any administration method may be used as long as the composition can reach the desired site. Specifically, the composition may be administered orally or parenterally through various routes, and non-limiting examples of the administration route may include ocular, oral, rectal, topical, intravenous, intraperitoneal, intramuscular, intraarterial, transdermal and/or intranasally injection, or through inhalation. Further, the composition may be administered by any device capable of moving the active substance to target cells.

In the present invention, the pharmaceutical composition for preventing or treating cancer may further include pharmaceutically acceptable carriers, excipients or diluents commonly used in the preparation of pharmaceutical compositions, and the carriers may include a non-natural carrier (non-naturally occurring carrier).

In the present invention, the term "pharmaceutically acceptable" means implying properties that are not toxic to cells or humans exposed to the composition.

More specifically, the pharmaceutical composition may be formulated in any form of powders, granules, tablets, capsules, suspensions, emulsions, syrups, aerosols, and other oral formulations, external preparations, suppositories, and sterile injectable solutions according to conventional methods. However, if the formulation is used for prevention or treatment of cancer in the art, it is not limited thereto.

The carriers, excipients and diluents able to be added in the pharmaceutical composition may include, for example, lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate, polycaprolactone (PCL; polycaprolactone), polylactic acid (PLA), poly-L-lactic acid (PLLA), mineral oil, and the like.

In the case of formulation, it can be prepared using diluents or excipients such as commonly used fillers, extenders, binders, wetting agents, disintegrants and surfactants.

Solid preparations for oral administration may include tablets, pills, powders, granules, capsules, and the like, and the solid preparations may be prepared by mixing at least one excipient such as starch, calcium carbonate, sucrose or lactose, gelatin, etc. with the extract and its fractions. Further, in addition of simple excipients, a lubricant such as magnesium stearate, talc, etc. may also be used.

Liquid preparations for oral administration include suspensions, liquid solutions, emulsions, syrups, etc. In addition to water and liquid paraffin, which are simple diluents commonly used in the art, various excipients such as wetting agents, sweeteners, fragrances and preservatives may be included. Preparations for parenteral administration may include sterile aqueous solutions, non-aqueous solutions, suspensions, emulsions, lyophilized preparations, suppositories, and the like. As the non-aqueous solvent and suspending agent, propylene glycol, polyethylene glycol, vegetable oil such as olive oil, and injectable ester such as ethyl oleate may be used. As a basic material for suppositories, witepsol, macrogol, tween 61, cacao butter, laurin, glycerogelatin, and the like, may be used.

In yet another aspect, the present invention provides a method for preparation of the extracellular vesicles according to the present invention. Specifically, the present invention may provide a preparation method of the extracellular vesicle, including: (a) inoculating human mesenchymal stem cells into a matrix gel for in vitro culture ("in vitro culture matrix gel"), which contains extracellular vesicles and polylactic acid; (b) subculture of the mesenchymal stem cells in a serum-free medium, in which extracellular vesicles derived from trophoblasts having immune-tolerant properties to secrete and express HLA-G, and extracellular vesicles secreted from human mesenchymal stem cells during hepatocyte differentiation are contained; (c) inoculating the sub-cultured mesenchymal stem cells on a culture plate and culturing the same in a serum-free medium to obtain a culture supernatant; and (d) centrifuging, filtering and separating the culture supernatant.

In the step (a), the extracellular vesicles and polylactic acid are mixed in a weight ratio of 1:1 to 1:20 to prepare an in vitro culture matrix gel. Further, in the step (a), the human mesenchymal stem cells may be inoculated at a density of 5,000 to 15,000 cells/cm$^2$.

The extracellular vesicles of step (a) may be prepared by, but not limited to, (a-1) freeze preservation of a human amniotic membrane and amniotic fluid-derived mesenchymal stem cells in a cryopreservation composition containing 5 to 50% (v/v) of extracellular vesicles derived from human mesenchymal stem cells; (a-2) inoculating the cryopreserved human amniotic membrane and amniotic fluid-derived mesenchymal stem cells on lower and upper plates of the co-culture plate; (a-3) obtaining a culture supernatant by co-culture in a serum-free medium; and (a-4) centrifuging and filtering the culture supernatant.

In this regard, the freeze preservation of the human mesenchymal stem cells in step (a-1) may be used for excluding heterologous antigens, and may include cryopreservation in a −80° C. cryogenic freezer. Further, the inoculation in step (a-2) includes inoculating the cells at a density of 18,000 to 22,000 cells/cm$^2$, respectively. Further, the co-culture of step (a-3) may be performed for 114 to 126 hours. Further, the culture supernatant in step (a-4) may be separated through centrifugation, followed by filtering using a 0.45 μm filter twice.

The extracellular vesicles of step (a) may contain: human chorionic gonadotropin (hCG) and placental growth factor (PlGF), which activate progesterone to promote mRNA expression of HLA-G protein in trophoblasts; and interleukin-1 beta (IL-1β), interleukin-6 (IL-6), interleukin-10 (IL-10), transforming growth factor-beta (TGF-β), interferon-gamma (IFN-γ) and tumor necrosis factor-alpha (TNF-α), which promote self-secretion of HLA-G protein in the trophoblasts.

The extracellular vesicles derived from the trophoblasts in step (b) may be prepared by, but not limited to, (b-1) inoculating trophoblasts into the in vitro culture matrix gel containing extracellular vesicles obtained through co-culture of the human amniotic membrane and amniotic fluid-derived mesenchymal stem cells in a serum-free medium and hyaluronic acid; (b-2) subculture of the trophoblasts in a serum-free medium; (b-3) inoculating the sub-cultured trophoblasts in a culture plate and culturing the same in a serum-free medium so as to obtain a culture supernatant; and (b-4) centrifuging, filtering, and separating the culture supernatant.

In this regard, the extracellular vesicles and hyaluronic acid in step (b-1) may be mixed in a weight ratio of 1:1 to 1:20 to prepare the in vitro culture matrix gel. Further, in step (b-1), the trophoblasts may be inoculated at a density of 5,000 to 15,000 cells/cm$^2$. Further, the trophoblasts sub-cultured in step (b-3) may be inoculated at a density of 10,000 to 20,000 cells/cm$^2$ on a general culture plate after washing, and then the culture supernatant is obtained after 90 to 100 hours of serum-free culture. Further, the culture supernatant in step (b-4) may be separated by centrifugation, followed by filtering using a 0.45 μm filter twice.

The trophoblast-derived extracellular vesicles of step (b) may include HLA-G1 and HLA-G5 proteins causing immune tolerance, progesterone to promote mRNA expression of HLA-G protein, as well as the human chorionic gonadotropin and placental growth factor that activate progesterone secretion in trophoblasts.

Further, the trophoblasts of step (b) may be prepared by, but not limited to, (b-1) inoculating the trophoblasts into the in vitro culture matrix gel, which contains the extracellular vesicles obtained by co-culture of human amniotic membrane and amniotic fluid-derived mesenchymal stem cells in a serum-free medium and hyaluronic acid; and (b-2) subculture of the trophoblasts in a serum-free medium.

In this case, the extracellular vesicles and hyaluronic acid of step (b-1) may be mixed in a weight ratio of 1:1 to 1:20 to prepare the in vitro culture matrix gel. Further, in step (b-1), the trophoblasts may be inoculated at a density of 5,000 to 15,000 cells/cm$^2$.

The trophoblasts of step (b) may secrete and express extracellular vesicles containing HLA-G1 and HLA-G5 proteins. Specifically, the extracellular vesicles containing both the HLA-G1 and HLA-G5 proteins may be continuously secreted and expressed.

The extracellular vesicles secreted during differentiation of hepatocytes in step (b) may be prepared by, but not limited to, (b-1) inoculating one or more selected from human bone marrow, fat, umbilical cord blood, placenta, amniotic epithelium, chorion, umbilical cord and amniotic fluid-derived mesenchymal stem cells onto a medium; (b-2) obtaining a culture supernatant by culturing the mesenchymal stem cells in a hepatocyte differentiation medium without serum; and (b-3) centrifuging, filtering and separating the culture supernatant.

Herein, the mesenchymal stem cells of step (b-1) may be inoculated at a density of 5×10$^4$ cells/cm$^2$. In addition, the culture supernatant in step (b-3) may be separated by performing centrifugation and filtering using a 0.45 μm filter twice.

DETAILED DESCRIPTION OF PREFERRED EMBODIMENTS OF INVENTION

Hereinafter, the configuration and effects of the present invention will be described in more detail through examples. These examples are for illustrative purposes only, and the scope of the present invention is not limited by these examples.

Example 1: Preparation of In Vitro Culture Matrix Gel for Trophoblasts to Induce Immune-Tolerant Characteristics A matrix gel was prepared for in vitro culture of trophoblasts, which is able to induce immune-tolerant properties.

More specifically, in order to exclude heterologous antigens that may be contained in extracellular vesicles, human amniotic membrane and amniotic fluid-derived mesenchymal stem cells were stored with a cryopreservation composition including the human mesenchymal stem cell-derived extracellular vesicles in replace of Fetal Bovine Serum (FBS), in a cryogenic freezer at −80° C. for 3 weeks. After thawing each of the stored stem cells, amnion-derived stem cells were dispensed on a lower plate of a multi-dish (ThermoFisher Scientific Inc., Rockford, Ill. USA, Cat. #140663) for co-culture, and the amniotic fluid-derived stem cells were dispensed on an upper insert of the above multi-dish with a serum-free DMEM/F12 medium at a density of 20,000 cells/cm$^2$, respectively, followed by co-culture in 5% CO$_2$ incubator at 37° C. for 120 hours. Thereafter, the collected culture supernatant was centrifuged and subjected to filtering using a 0.45 μm filter twice. From the separated human amniotic fluid and amniotic membrane-derived stem cells, co-cultured extracellular vesicles were harvested. Further, as a result of analyzing whether the obtained extracellular vesicles contain proteins expected to be necessary for continuous HLA-G secretion expression in trophoblasts by the present inventors by means of ELISA kit, it was confirmed that cytokines such as IL-1β, IL-6, IL-10, TGF-β, IFN-γ and TNF-α secreted in the interaction between hCG, PlGF and trophoblasts, which promote expression of progesterone directly associated with promotion of HLA-G protein mRNA expression in the trophoblasts, and decidual immune cells were all contained in the extracellular vesicles (Table 1).

TABLE 1

Concentrations of major proteins contained in co-cultured extracellular vesicles of human amniotic membrane and amniotic fluid-derived mesenchymal stem cells

| Proteins | Concentration (pg/ml) |
| --- | --- |
| IL-1β | 8.2 ± 2.4 |
| IL-6 | 5,626.5 ± 142.3 |
| IL-10 | 8.1 ± 3.6 |
| TNF-α | 58.6 ± 11.1 |
| TGF-β | 2,350.1 ± 100.2 |
| IFN-γ | 12.1 ± 1.5 |
| hCG | 55.0 ± 3.6 |
| PlGF | 390.2 ± 9.7 |
| Progesterone | Not detected |

After adding hyaluronic acid powder to the co-cultured extracellular vesicle solution of human amniotic fluid and amniotic membrane-derived stem cells collected by the above method to reach pH 6.6 to 6.8 and then mixing well with a vortex, the prepared in vitro culture matrix gel was dispensed on a culture plate, followed by shaking the same on a vibrator to spread evenly. Then, after dispensing trophoblasts, a growth rate of the trophoblasts and a concentration of HLA-G protein contained in the culture supernatant were measured while conducting subculture in a serum-free DMEM/F12K medium every 5 to 7 days.

As a result, as shown in FIG. 3, it was confirmed that the trophoblasts cultured in the serum-free DMEM/F12K medium by dispensing the same at the same cell density into a culture plate coated with a matrix gel for in vitro culture had a growth rate increased as the subculture proceeded and, when the subculture progressed to 5 passages, the growth rate was excellent more than about 5 times, as compared to the control group dispensed on a typical culture plate and cultured in 10% FBS containing DMEM/F12K medium.

From the above result, it was confirmed that the in vitro culture matrix gel of the present invention could desirably replace fetal bovine serum (FBS) in the proliferation of trophoblasts (FIG. 3).

Further, in order to confirm whether the trophoblasts cultured on the in vitro culture matrix gel could continuously secrete target proteins, a concentration of soluble HLA-G (sHLA-G) protein in the obtained culture supernatant in each subculture was measured during subculture.

More specifically, the concentration of sHLA-G protein was measured in the culture supernatant obtained in the subculture of trophoblasts by means of HLA-G ELISA kit (LS Bio, LS-F22591) using a MEMG/9 antibody that binds to the "β2m (beta 2-microglobulin)" portion commonly present in HLA-G1 and HLA-G5 proteins.

As a result, as shown in FIG. 4, it was confirmed that the concentration of sHLA-G protein in the culture supernatant of trophoblasts cultured in the in vitro culture matrix gel gradually increased as the subculture proceeded. On the contrary, in the case of the trophoblasts cultured in a typical culture plate, the concentration of sHLA-G contained in the culture supernatant gradually decreased as the subculture proceeded (FIG. 4).

From the above result, it was confirmed that the in vitro culture matrix gel of the present invention was superior for inducing the continuous secretion of HLA-G protein, which is an immune-tolerant protein, to the normal culture plate cultivation.

Example 2: Preparation of Immune-Tolerized Trophoblast-Derived Extracellular Vesicles for Transcription of Immune Tolerant Properties into Target Cell By allowing the extracellular vesicles obtained in Example 1 to be transcribed in target cells, a culture method capable of having immune-tolerant properties by HLA-G protein was devised.

Specifically, the trophoblasts cultured in the in vitro culture matrix gel prepared in Example 1 were dispensed in a serum-free DMEM/F-12K medium at a density of 15,000 cells/cm$^2$ and cultured in a 5% $CO_2$ incubator at 37° C. for 96 hours. The culture supernatant collected after culture was separated by centrifugation and filtering using a 0.45 μm filter twice, so as to obtain extracellular vesicles derived from the trophoblasts having immune-tolerant properties by HLA-G protein. Further, whether the obtained extracellular vesicles contained progesterone, hCG, PlGF and HLA-G5 proteins, which are expected to be necessary for transcription of immune-tolerant properties by the present inventors in order to sustain HLA-G secretion and expression even in target cells, was analyzed by means of ELISA kit. More specifically, the HLA-G5 concentration was measured using an ELISA kit (MyBiosource, MBS267094) which used an "5A6G7" antibody binding to the "Intron 4" portion present only in the HLA-G5 protein.

TABLE 2

Concentrations of major proteins required for transcription of immune-tolerant properties to secrete and express HLA-G protein contained in human trophoblast-derived extracellular vesicles

| Proteins | Concentration (ng/ml) |
| --- | --- |
| hCG | 26.46 ± 5.17 |
| PlGF | 6.78 ± 1.22 |
| Progesterone | 20.52 ± 1.45 |
| HLA-G5 (IU/ml) | 89.74 ± 0.56 |

As a result, as shown in Table 2, the extracellular vesicles derived from trophoblasts obtained from the in vitro culture matrix gel contained all of HLA-G5, progesterone, hCG and PlGF proteins, whereas these proteins were not detected in the extracellular vesicles obtained from the normal culture plate (Table 2).

From the above result, it was confirmed that the in vitro culture matrix gel of the present invention is superior to the culture in a general culture plate in terms of inducing transcription effects of immune-tolerant properties.

Example 3: Preparation of Anti-Cancer Extracellular Vesicles Containing LDHB and PGC-1α

In order to prepare anticancer extracellular vesicles of the present invention, the present experiment was conducted.

More specifically, in order to induce the secretion of LDHB-containing extracellular vesicles in target cells, a kind of mesenchymal stem cells selected from human bone marrow, fat, umbilical cord blood, placenta, amniotic epithelium, chorion, umbilical cord and amniotic fluid-derived mesenchymal stem cells were inoculated into a hepatocyte differentiation initiating medium, which contains 60% DMEM LG (Gibco, 11885) medium, 40% MCDB 201 (Signa, M6770), 20 ng/ml EGF, 10 ng/ml bFGF, 10 ng/ml BMP-4 and 1% penicillin/streptomycin at a density of $5\times10^4$ cells/cm$^2$, and then cultured in an incubator under environments of 37° C. and 5% $CO_2$. Thereafter, the mesenchymal stem cells were transferred to a hepatocyte differentiation medium (containing 60% DMEM LG (Gibco, 11885) medium, 40% MCDB 201 (Signa, M6770), 20 ng/ml HGF, 10 ng/ml bFGF and 1% penicillin/streptomycin), followed by inducing differentiation for 7 days or 14 days. The collected culture supernatant was subjected to centrifugation and filtering using a 0.45 μm filter twice. As a result, the extracellular vesicles secreted during hepatocyte differentiation of human mesenchymal stem cells were isolated and harvested.

In addition, in order to prepare immune-tolerized extracellular vesicles containing LDHB, PGC-1α and PGC-1α mRNA transcription promoters in target cells, polylactic acid was added in replace of hyaluronic acid to the in vitro culture matrix gel prepared in Example 1 for inducing PGC-1α secretion by lactate stimulation, thus producing a polylactic acid-containing in vitro culture matrix gel. The produced polylactic acid-containing in vitro culture matrix gel was dispensed on a culture plate, followed by inoculating human amniotic fluid-derived mesenchymal stem cells (hAF-MSCs) at a density of $1.5\times10^4$ cells/cm$^2$ thereon. Then, the above inoculated gel was cultured in each serum-free DMEF/F-12 medium containing 10% v/v of the trophoblast-derived extracellular vesicles having induced immune-tolerant properties in Example 2, which always secrete and express HLA-G protein, and the extracellular vesicles secreted during hepatocyte differentiation of human mesenchymal stem cells in Example 3, respectively. In order to stimulate movement and further promote the expression of PGC-1α in target cells, the culture was performed using a plate shaker installed in an incubator under environments of 37° C. and 5% $CO_2$.

After subculture to 3 passages, the cultured hAF-MSC was washed, inoculated on a normal plate without the matrix gel at a density of $2.0\times10^4$ cells/cm$^2$, and then cultured with the serum-free DMEM/F-12 medium in a $CO_2$ 5% incubator at 37° C. for 120 hours. The collected culture supernatant was centrifuged and subjected to filtering using a 0.45 μm filter twice in order to obtain extracellular vesicles with induced immune-tolerant properties for cancer treatment, followed by measurement using an ELISA kit.

As a result, as shown in Table 3, it was confirmed that HLA-G5 protein having immune-tolerant properties, hCG and PlGF proteins essential for inducing continuous secretion of HLA-G protein in target cells, LDHB as an enzyme to convert lactate into pyruvate in cancer cells and PGC-1α to promote expression of the same, and CaMK and MEF2 proteins to promote PGC-1α mRNA expression and transcription in target cells and cancer cells, were all contained (Table 3).

TABLE 3

Concentrations of major proteins in immune-tolerized extracellular vesicles for cancer treatment

| Proteins | Concentration (ng/ml) |
|---|---|
| hCG | 26.46 ± 5.17 |
| PlGF | 6.78 ± 1.22 |
| Progesterone | Not detected |
| sHLA-G | 16.22 ± 0.89 |
| HLA-G5 (IU/ml) | 68.37 ± 11.16 |
| LDHB | 39.81 ± 0.38 |
| PGC-1α | 13.55 ± 1.71 |
| CaMK1B | 27.11 ± 0.69 |
| CaMK2B | 11.16 ± 0.58 |
| CaMK5 | 9.46 ± 0.65 |
| MEF2B | 29.56 ± 1.49 |
| MEF2C | 5.33 ± 0.23 |
| cAMP | 8.39 ± 0.76 |

From the above results, it was expected that the extracellular vesicles obtained through culture may be used as a pharmaceutical composition for cancer treatment because of anticancer active ingredients contained therein.

Example 4: Verification of In Vitro Anticancer Efficacy of Anticancer Extracellular Vesicles Containing LDHB and PGC-1α

In order to verify anticancer efficacy of the extracellular vesicles, an extracellular vesicle absorption experiment was performed on a breast cancer cell line.

More specifically, in order to confirm whether the extracellular vesicles are absorbed by cancer cells, an extracellular vesicle absorption experiment was performed on two types of breast cancer cell lines. The extracellular vesicles were labeled with PKH24 (Sigma) fluorescent dye, used for treatment of MDA-MB231 and MCF7 human breast cancer cell lines, and cultured for 24 hours, followed by flow cytometry to confirm the breast cancer cell lines absorbing the anticancer extracellular vesicles of the present invention.

TABLE 4

Cancer cell absorption rate of anticancer extracellular vesicles and changes in lactate/pH

| Cancer cell line | | MDA-MB231 | MCF7 |
|---|---|---|---|
| Anticancer extracellular vesicles uptake (%) | | 95.69 ± 3.87% | 97.13 ± 5.29% |
| Lactate concentration | Control group | 16.74 ± 1.42 mM | 22.36 ± 1.78 mM |
| | Test group | 0.57 ± 0.11 mM | 0.89 ± 0.16 mM |
| pH | Control group | 6.3 | 6.2 |
| | Test group | 7.2 | 7.4 |

As a result, as shown in Table 4, it could be confirmed that the anticancer extracellular vesicles of the present invention were absorbed in 95% or more of the breast cancer cell lines.

Further, in order to verify the anticancer efficacy of the extracellular vesicles, changes in lactate and pH of the culture supernatant of the breast cancer cell line were measured.

As shown in Table 4, as a result of measuring lactate and pH in the culture supernatant, it could be confirmed that the lactate concentration was considerably lower than that of the control group not treated with extracellular vesicles, and that the pH was maintained above 7.0.

From the above result, it was confirmed that the extracellular vesicles of the present invention are effectively absorbed by the cancer cell line, and PGC-1α, which increases the expression of LDHB enzyme and LDHB enzyme contained in the extracellular vesicles, and CaMK, MEF2 and cAMP, which promote intracellular transcription of PGC-1α, are delivered to cancer cells, thereby achieving effects of normalizing energy metabolism of cancer cells through cancer cell immunity evasion, as well as efficient inhibition of the surrounding microenvironments such as high lactate concentration and low pH.

Example 5: Verification of In Vivo Anticancer Efficacy of Anticancer Extracellular Vesicles Containing LDHB and PGC-1α

In order to verify the anticancer efficacy of the extracellular vesicles, a tumor size reduction experiment was performed after injection of extracellular vesicles in a mouse cancer model.

More specifically, 3-month-old BALB/c lineage mice were separated into a control group and an experimental group by 5 mice each, and then 100 μl of a cultured colon cancer cell line (CT-26 cells, musculus colon carcinoma) at a density of 2×10$^5$ cells/RPMI 1640 medium was subcutaneously injected on one side of the left or right flank of each mouse in the experimental group. After 4 weeks of injection of the tumor cell line, the control group was intraperitoneally injected with 200 μl of PBS at an interval of 3 days, and the experimental group was intraperitoneally injected with 200 μl of the extracellular vesicles for cancer treatment of the present invention at an interval of 3 days, respectively, followed by measuring a volume of the tumor at an interval of 10 days.

As a result, as shown in FIG. 5, it was confirmed that the treatment group injected with the anticancer extracellular vesicles has a tumor volume significantly decreased compared to the control group.

Accordingly, it could be demonstrated that the extracellular vesicles of the present invention have anticancer efficacy to inhibit tumor growth.

From the above description, those skilled in the art to which the present invention pertains will understand that the present invention can also be implemented in other specific forms without changing the technical spirit or essential features thereof. In this regard, the embodiments described above are proposed for illustrative purpose in all respects and should be understood as non-limiting. The scope of the present invention should be construed that all changes or modifications derived from the meaning and scope of the claims to be described later and equivalent concepts thereof, rather than the above detailed description, will be included in the scope of the present invention.

The invention claimed is:

1. Extracellular vesicles, comprising:
   (i) lactate dehydrogenase B(LDHB);
   (ii) peroxisome proliferator-activated receptor gamma co-activator 1-alpha (PGC-1α); and
   (iii) calcium-calmodulin activated kinases type 1B (CaMK1B), calcium-calmodulin activated kinases type 2B (CaMK2B), calcium-calmodulin activated kinase type 5 (CaMK5), myocyte specific enhancer 2B (MEF2B), myocyte specific enhancer 2C (MEF2C) and cyclin adenosine monophosphate (cAMP),
   wherein the extracellular vesicles are prepared by:
   (a-1) inoculating human mesenchymal stem cells into a matrix gel for in vitro culture ("in vitro culture matrix gel"), which contains extracellular vesicles obtained through co-culture of human amniotic membrane and amniotic fluid-derived mesenchymal stem cells and polylactic acid;
(a-2) preparing a subculture of the mesenchymal stem cells in a serum-free medium, in which extracellular vesicles derived from trophoblasts having immune-tolerant properties to secrete and express HLA-G, and extracellular vesicles secreted during differentiation of human mesenchymal stem cells into hepatocyte are contained;
(a-3) inoculating the sub-cultured mesenchymal stem cells on a culture plate and culturing the same in a serum-free medium to obtain a culture supernatant; and
(a-4) centrifuging, filtering and separating the culture supernatant;
wherein the extracellular vesicles derived from trophoblasts are prepared by:
(b-1) inoculating trophoblasts into the in vitro culture matrix gel containing extracellular vesicles obtained through co-culture of the human amniotic membrane and amniotic fluid-derived mesenchymal stem cells in a serum-free medium and hyaluronic acid;
(b-2) preparing a subculture of the trophoblasts in a serum-free medium;
(b-3) inoculating the sub-cultured trophoblasts in a culture plate and culturing the same in a serum-free medium so as to obtain a culture supernatant; and
(b-4) centrifuging, filtering and separating the culture supernatant; and
wherein the extracellular vesicles secreted during differentiation of hepatocytes are prepared by:
(c-1) culturing one or more selected from human bone marrow, fat, umbilical cord blood, placenta, amniotic epithelium, chorion, umbilical cord and amniotic fluid-derived mesenchymal stem cells in a hepatocyte differentiation initiating medium which contains epidermal growth factor (EGF), basic fibroblast growth factor (bFGF) and bone morphogenetic protein 4 (BMP-4); and
(c-2) obtaining a culture supernatant by culturing the cultured mesenchymal stem cells in a hepatocyte differentiation medium which contains hepatocyte growth factor (HGF) and basic fibroblast growth factor (bFGF) for 7 days to 14 days; and
(c-3) centrifuging, filtering and separating the obtained culture supernatant.

2. The extracellular vesicles according to claim 1, further comprising:
(iv) HLA-G1 and HLA-G5 proteins, and
(v) human chorionic gonadotropin (hCG) and placental growth factor (PlGF).

3. A pharmaceutical composition for treatment of cancer, comprising the extracellular vesicles according to claim 1.

4. A method for production of the extracellular vesicles according to claim 1, the method comprising:
(i) inoculating human mesenchymal stem cells into a matrix gel for in vitro culture ("in vitro culture matrix gel"), which contains extracellular vesicles obtained through co-culture of human amniotic membrane and amniotic fluid-derived mesenchymal stem cells and polylactic acid;
(ii) preparing a subculture of the mesenchymal stem cells in a serum-free medium, in which extracellular vesicles derived from trophoblasts having immune-tolerant properties to secrete and express HLA-G, and extracellular vesicles secreted during differentiation of human mesenchymal stem cells into hepatocyte are contained;
(iii) inoculating the sub-cultured mesenchymal stem cells on a culture plate and culturing the same in a serum-free medium to obtain a culture supernatant; and
(iv) centrifuging, filtering and separating the culture supernatant,
wherein the extracellular vesicles derived from trophoblasts are prepared by:
(a-1) inoculating trophoblasts into the in vitroculture matrix gel containing extracellular vesicles obtained through co-culture of the human amniotic membrane and amniotic fluid-derived mesenchymal stem cells in a serum-free medium and hyaluronic acid;
(a-2) subculture of the trophoblasts in a serum-free medium;
(a-3) inoculating the sub-cultured trophoblasts in a culture plate and culturing the same in a serum-free medium so as to obtain a culture supernatant; and
(a-4) centrifuging, filtering and separating the culture supernatant; and
wherein the extracellular vesicles secreted during differentiation of hepatocytes are prepared by:
(b-1) culturing one or more selected from human bone marrow, fat, umbilical cord blood, placenta, amniotic epithelium, chorion, umbilical cord and amniotic fluid-derived mesenchymal stem cells in a hepatocyte differentiation initiating medium which contains epidermal growth factor (EGF), basic fibroblast growth factor (bFGF) and bone morphogenetic protein 4 (BMP-4);
(b-2) obtaining a culture supernatant by culturing the cultured mesenchymal stem cells in a hepatocyte differentiation medium which contains hepatocyte growth factor (HGF) and basic fibroblast growth factor (bFGF) for 7 days to 14 days; and
(b-3) centrifuging, filtering and separating the obtained culture supernatant.

5. The method according to claim 4, wherein the extracellular vesicles of step (i) are prepared by:
respective freeze preservation of the human amniotic membrane and amniotic fluid-derived mesenchymal stem cells in a cryopreservation composition containing 5 to 50% (v/v) of extracellular vesicles derived from human mesenchymal stem cells;
inoculating the cryopreserved human amniotic membrane and amniotic fluid-derived mesenchymal stem cells on lower and upper plates of the co-culture plate;
obtaining a culture supernatant by co-culture in a serum-free medium; and
centrifuging and filtering the culture supernatant.

6. The method according to claim 4, wherein the extracellular vesicles of step (i) contain:
human chorionic gonadotropin (hCG) and placental growth factor (PlGF), which activate progesterone to promote mRNA expression of HLA-G protein in trophoblasts; and
interleukin-1 beta (IL-1β), interleukin-6 (IL-6), interleukin-10 (IL-10), transforming growth factor-beta (TGF-β), interferon-gamma (IFN-γ) and tumor necrosis factor-alpha (TNF-α), which promote autonomous secretion of HLA-G protein in the trophoblasts.

7. The method according to claim 4, wherein the trophoblast-derived extracellular vesicles of step (ii) contain:
HLA-G1 and HLA-G5 proteins causing immune tolerance;

progesterone promoting mRNA expression of HLA-G protein; and human chorionic gonadotropin and placental growth factor that activate secretion of progesterone in trophoblasts.

8. The method according to claim 4, wherein the trophoblasts of step (ii) are prepared by:

inoculating the trophoblasts into the in vitro culture matrix gel, which contains the extracellular vesicles obtained through co-culture of human amniotic membrane and amniotic fluid-derived mesenchymal stem cells in a serum-free medium and hyaluronic acid; and subculture of the trophoblasts in a serum-free medium.

9. The method according to claim 4, wherein the Trophoblasts of step (ii) secrete and express extracellular vesicles containing HLA-G1 and HLA-G5 proteins.

* * * * *